(12) United States Patent
Arai et al.

(10) Patent No.: US 10,856,726 B2
(45) Date of Patent: Dec. 8, 2020

(54) MEDICAL SUPPORT ARM APPARATUS

(71) Applicant: SONY CORPORATION, Tokyo (JP)

(72) Inventors: Jun Arai, Kanagawa (JP); Yasuhisa Kamikawa, Tokyo (JP); Kiyokazu Miyazawa, Kanagawa (JP); Yohei Kuroda, Tokyo (JP); Yasuhiro Matsuda, Tokyo (JP); Tetsuharu Fukushima, Tokyo (JP)

(73) Assignee: SONY CORPORATION, Tokyo (JP)

(*) Notice: Subject to any disclaimer, the term of this patent is extended or adjusted under 35 U.S.C. 154(b) by 315 days.

(21) Appl. No.: 15/554,754

(22) PCT Filed: Feb. 2, 2016

(86) PCT No.: PCT/JP2016/052983
§ 371 (c)(1),
(2) Date: Aug. 31, 2017

(87) PCT Pub. No.: WO2016/152255
PCT Pub. Date: Sep. 29, 2016

(65) Prior Publication Data
US 2018/0042464 A1 Feb. 15, 2018

(30) Foreign Application Priority Data
Mar. 25, 2015 (JP) ................................. 2015-062159

(51) Int. Cl.
A61B 1/00 (2006.01)
A61B 17/02 (2006.01)
(Continued)

(52) U.S. Cl.
CPC ........ *A61B 1/00149* (2013.01); *A61B 1/0014* (2013.01); *A61B 17/02* (2013.01);
(Continued)

(58) Field of Classification Search
CPC ..... A61B 1/00149; A61B 34/30; A61B 34/70; A61B 90/00; A61B 90/50
See application file for complete search history.

(56) References Cited

U.S. PATENT DOCUMENTS 8,942,828 B1    1/2015  Schecter
2010/0090691 A1* 4/2010  Kishida .................. G01R 33/04
                                                    324/244
(Continued)

FOREIGN PATENT DOCUMENTS

JP    2008-259835 A    10/2008
JP    2009-34744 A     2/2009
(Continued)

OTHER PUBLICATIONS

International Search Report dated Mar. 22, 2016 in PCT/JP2016/052983.

*Primary Examiner* — Samuel S Hanna
(74) *Attorney, Agent, or Firm* — Xsensus LLP

(57) ABSTRACT

The present invention aims to make it capable of holding organs more safely.
Provided is a medical support arm apparatus, including: an arm unit (510) whose driving is controlled by force control; and a retractor, provided on a front end of the arm unit (510), that holds an organ of a patient during surgery.

11 Claims, 11 Drawing Sheets

(51) Int. Cl.
  *A61B 34/30* (2016.01)
  *A61B 90/50* (2016.01)
  *A61B 90/00* (2016.01)
  *B25J 9/16* (2006.01)
  *A61B 34/00* (2016.01)
  *A61B 1/313* (2006.01)

(52) U.S. Cl.
  CPC .............. *A61B 34/30* (2016.02); *A61B 34/70* (2016.02); *A61B 90/00* (2016.02); *B25J 9/1633* (2013.01); *A61B 1/00133* (2013.01); *A61B 1/3132* (2013.01); *A61B 90/50* (2016.02); *A61B 2090/064* (2016.02)

(56) References Cited

U.S. PATENT DOCUMENTS

2011/0264108 A1*  10/2011  Nowlin .................. B25J 9/1689
                                                            606/130
2014/0148951 A1*  5/2014   Saen ...................... B25J 13/083
                                                            700/259

FOREIGN PATENT DOCUMENTS

| JP | 2009-34744 A5 | 2/2009 | |
|---|---|---|---|
| JP | 2010-511487 A | 4/2010 | |
| JP | 2012-210392 A | 11/2012 | |
| JP | 2015-2922 A | 1/2015 | |
| WO | WO 2008/093796 A1 | 8/2008 | |
| WO | WO-2008093796 A1 * | 8/2008 | ............. A61B 17/02 |

* cited by examiner

MEDICAL SUPPORT ARM APPARATUS

TECHNICAL FIELD

The present disclosure relates to a medical support arm apparatus.

BACKGROUND ART

In endoscopic surgery, surgery is performed without a surgeon inserting his or her hands directly into a body cavity of a patient, but instead by inserting specialized treatment tools into the body cavity from small insertion openings (wounds) provided in the body wall of the patient, and operating the treatment tools from outside the body cavity. At this point, to secure a work space around the operating site, in some cases it becomes necessary to hold objects such as internal organs and tissues inside the body cavity or the body wall (hereinafter collectively designated organs). Accordingly, various technologies are being developed as technologies for holding the organs of a patient to secure a work space during surgery.

For example, Patent Literature 1 discloses a support apparatus that, in laparoscopic surgery, supports a retractor which is inserted into the body cavity of the patient together with a laparoscope and which holds an internal organ or tissue inside the body cavity to secure a work space. With this support apparatus, a surgeon (user) operates a control handle provided on the support apparatus, and is thereby able to move the position of the retractor and move the position of the internal organ or tissue inside the body cavity, and form a work space for performing surgery inside the body cavity.

As another example, Patent Literature 2 discloses a treatment apparatus which is used in endoscopic surgery. The treatment apparatus is provided with a first medical instrument which is installed inside a body cavity of a patient and which is magnetic, and a second medical instrument which is installed outside the body and which induces the first medical instrument by magnetic interaction through a body wall and/or an internal organ to be held. According to this treatment apparatus, by operating the second medical instrument to induce the first medical instrument, it becomes possible to retract the body wall and/or internal organ in an arbitrary direction, and form a work space for performing surgery inside the body cavity.

CITATION LIST

Patent Literature

Patent Literature 1: JP 2010-511487T
Patent Literature 2: JP 2008-259835A

DISCLOSURE OF INVENTION

Technical Problem

However, with the support apparatus described in Patent Literature 1, operations on the control handle are transmitted to the retractor and the positioning of the retractor is conducted by mechanical elements such as wires, pulleys, and pistons. In other words, the support apparatus described in Patent Literature 1 may be considered to be a support apparatus in which the operation of the retractor is controlled so that the retractor is positioned at a certain position indicated by a user via the control handle, or in other words, the operation of the retractor is controlled by what is called position control. With a support apparatus according to such position control, the retractor continues to remain at the indicated position until a new instruction is given. Thus, in a case in which the retractor contacts an internal organ or the like while the retractor is moving, or in a case in which an internal organ or the like moves due to the respiration, heartbeat, or the like of the patient while that internal organ or the like is being held, for example, there is a risk of the retractor damaging the internal organ or the like.

Also, with the treatment apparatus described in Patent Literature 2, since only magnetic instruments can be used as the first medical instrument and the second medical instrument, general-purpose instruments cannot be used. Also, with the treatment apparatus described in Patent Literature 2, since the position of the first medical instrument inside the body cavity is controlled from outside the body by magnetic interaction, positioning the first medical instrument with high precision is considered to be difficult. Consequently, as a result, there is a risk of the first medical instrument moving unintentionally and damaging an internal organ or the like inside the body cavity.

In this way, as a technology for holding the organs of a patient during surgery, there is demand for a technology capable of holding organs more safely. Accordingly, the present disclosure proposes a new and improved medical support arm apparatus capable of holding organs more safely.

Solution to Problem

According to the present disclosure, there is provided a medical support arm apparatus, including: an arm unit whose driving is controlled by force control; and a retractor, provided on a front end of the arm unit, that holds an organ of a patient during surgery.

According to the present disclosure, a retractor that holds an organ of a patient during surgery is supported by an arm unit of a support arm apparatus, and the driving of the arm unit is controlled by force control. According to force control, it is possible to realize control that limits force, such as causing the arm unit to operate with a set threshold value on the force acting on the retractor, for example. Consequently, it is possible to prevent an organ from being subjected to an excessive force by the retractor, and safer surgery may be realized.

Advantageous Effects of Invention

According to the present disclosure as described above, it is possible to hold organs more safely. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
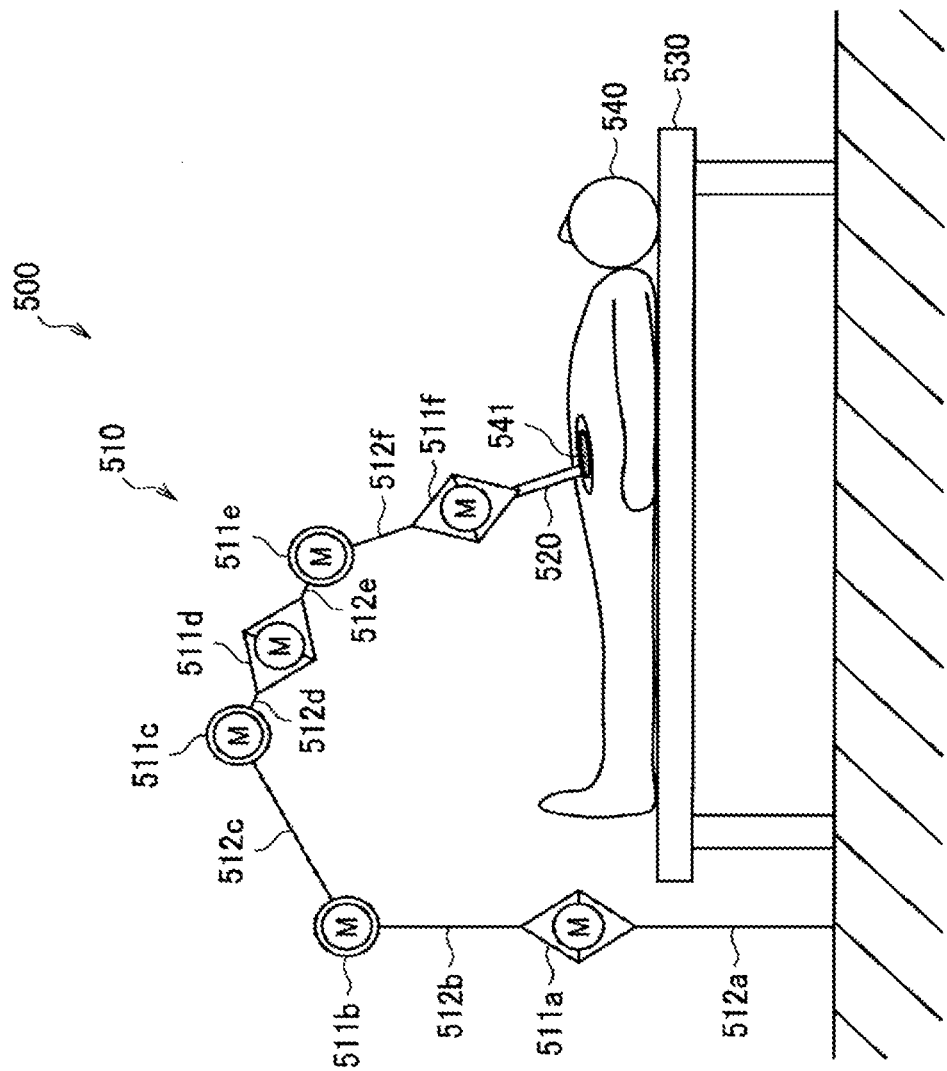
FIG. 1 is a schematic diagram illustrating a state of surgery using a support arm apparatus according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. Overview of surgery using support arm apparatus
2. Configuration of support arm apparatus
2-1. Overall configuration
2-2. Configuration of actuator
3. Control method of support arm apparatus
4. Exemplary application of support arm apparatus to surgery
4-1. Exemplary application to abdominal surgery
4-2. Exemplary application to endoscopic surgery
5. Modification
6. Supplemental remarks (1. Overview of Surgery Using Support Arm Apparatus)

Before describing in detail a configuration of a support arm apparatus according to a preferred embodiment of the present disclosure, to further clarify the present disclosure, an overview of surgery using a support arm apparatus according to the present embodiment will be described.

A state of surgery using a support arm apparatus according to an embodiment of the present disclosure will be described with reference to FIG. 1. FIG. 1 is a schematic diagram illustrating a state of surgery using a support arm apparatus according to an embodiment of the present disclosure.

As an example, FIG. 1 illustrates a state in which a support arm apparatus 500 according to the present embodiment is used to perform endoscopic surgery on a patient 540 lying on an operating table 530. In endoscopic surgery, multiple small insertion openings are provided in the body wall of a patient, and from one of the insertion openings, an endoscope for observing the operating site is inserted. Also, from another insertion opening, a treatment tool such as a scalpel for performing various treatments on the operating site is inserted. In addition, from yet another insertion opening, a retractor 520 that holds an organ 541 inside the body cavity of the patient 540 to secure a work space around the operating site is inserted. A surgeon operates the treatment tool while looking at a picture of operating site taken by the endoscope, and various treatments are performed on the operating site. Note that in FIG. 1, for the sake of simplicity, the surgeon, the treatment tool operated by the surgeon, and endoscope are omitted from illustration.

The support arm apparatus 500 according to the present embodiment is for supporting the retractor 520 that holds the organ 541. Note that in this specification, "organ" is a collective term that refers to anything which may be held by the retractor 520, such as any of the patient's various internal organs, tissues, or body wall. The internal organs may include any of various types of internal organs, such as the stomach, intestines, and liver, for example. Also, the tissues may include blood vessels and the like, for example.

In FIG. 1, for the sake of simplicity, among the configuration of the support arm apparatus 500, only an arm unit 510 and the retractor 520 attached to the front end of the arm unit 510 are illustrated. In actuality, on the base end side of the arm unit 510, a base unit that supports the arm unit 510 may be provided. Furthermore, the support arm apparatus 500 may be provided with a control device that controls the operation of the support arm apparatus 500. Note that a specific configuration of the support arm apparatus 500 will be described in detail in (2. Configuration of support arm apparatus) below.

The arm unit 510 is provided with multiple joint units 511a, 511b, 511c, 511d, 511e, and 511f, multiple links 512a, 512b, 512c, 512d, 512e, and 512f rotatably joined to each other by the joint units 511a to 511e, and the retractor 520 rotatably attached to the front end of the arm unit 510 via the joint unit 511f.

Each of the joint units 511a to 511f is provided with an actuator 430 illustrated in FIG. 7 to be described later, and the joint units 511a to 511f are configured to be rotatable about a certain rotation axis by the driving of the actuator 430. By controlling the driving of the actuator 430 with the above control device, the rotational angle of each of the joint units 511a to 511f is controlled, and the driving of the arm unit 510 is controlled. Note that in the present embodiment, the driving of the arm unit 510 is controlled by force control.

In the support arm apparatus 500, six degrees of freedom with respect to the driving of the arm unit 510 are realized by the six joint units 511a to 511f. By configuring the arm unit 510 to have six degrees of freedom, the retractor 520 can be moved freely within the movable range of the arm unit 510. With this arrangement, the angle at which to insert the retractor 520 into the body cavity of the patient is not limited, and the usability of the support arm apparatus 500 is improved.

The retractor 520 is a tool that holds the organ 541 of the patient 540 during surgery. When performing surgery, as illustrated in FIG. 1, the retractor 520 provided on the front end of the arm unit 510 is inserted into the body cavity of the patient 540, and the position and the orientation of the arm unit 510 and the retractor 520 are controlled by the support arm apparatus 500 so that the organ 541 inside the body cavity of the patient 540 is held by the retractor 520. By having the organ 541 inside the body cavity be held by the retractor 520, a work space around the operating site on which the surgeon is to perform treatment is secured.

Note that in FIG. 1, for the sake of simplicity, the specific shape of the retractor 520 is omitted from illustration, but in actuality, a suitable retractor 520 may be selected and used from among various types of retractors 520 having a variety of shapes, in accordance with the surgical technique and the object to be held. In the present embodiment, the type of retractor 520 supported by the support arm apparatus 500 is not limited, and any of various types of retractors 520 may be used in accordance with the surgical technique and the object to be held. A specific example of the retractor 520 will be described in detail in (2. Configuration of support arm apparatus) below.

The above thus describes a state of surgery using a support arm apparatus according to the present embodiment with reference to FIG. 1. Note that in FIG. 1, a case in which the support arm apparatus 500 is applied to endoscopic surgery is illustrated as an example, but the present embodiment is not limited to such an example, and the support arm apparatus 500 may also be applied to abdominal surgery. During abdominal surgery, the support arm apparatus 500 may use the retractor 520 to hold an organ inside the body cavity similarly to endoscopic surgery, but may also hold the body wall opened at an abdominal incision so as to spread the body wall outward and secure an opening at the abdominal incision.

So far, this has typically required a dedicated physician (assistant) to operate the retractor 520 and hold the organ 541 during surgery. Since the assistant must continually support the retractor 520 until the surgeon finishes treatment, the work has posed a large burden. If surgery carries on for a long time, the assistant may make a mistake when operating the retractor 520 due to fatigue, and there is an increased danger of an accident occurring, such as the organ 541 being damaged by the retractor 520.

Also, in the middle of surgery, in some cases it is necessary to move the position of the organ 541 appropriately in response to an instruction from the surgeon, for example. In such cases, the assistant receives the instruction verbally from the surgeon, and operates the retractor 520 to move the position of the organ 541. Such verbal communication does not necessarily guarantee that the surgeon's intent will be transmitted perfectly, and contributes to lowering the efficiency of surgery.

On the other hand, in the present embodiment, as described above, the retractor 520 is supported by the support arm apparatus 500. By substituting the work that has been conducted manually so far with the support arm apparatus 500, the great burden that has been imposed on an assistant holding the organ 541 can be resolved. Also, the occurrence of mistakes caused by the fatigue of the assistant also can be prevented. In addition, since the surgeon (user) is able to operate the support arm apparatus 500 him- or herself and move the position of the organ 541, communication between the surgeon and an assistant becomes unnecessary, and surgery can be made more efficient.

Herein, the technology itself of attempting to hold the retractor 520 with a support arm apparatus has also been proposed in the past (for example, see Patent Literature 1 described above). However, existing support arm apparatuses as exemplified by Patent Literature 1 described above control the operation of the retractor 520 by what is called position control. With position control, operation is controlled so that the retractor 520 continues to remain at an indicated position.

However, in the middle of surgery, the position of the organ 541 of the patient 540 is not necessarily constant. For example, the position of the organ 541 may change slightly in response to vital reactions of the patient 540, such as respiration and heartbeat. With a support arm apparatus that controls the operation of the retractor 520 by position control, the retractor 520 continues to remain at a certain position even in a case in which the position of the organ 541 changes, and thus there is a risk of the organ 541 being damaged by the retractor 520. Also, in a case of attempting to move the retractor 520 to a certain position, since the retractor 520 moves to the indicated position even if the organ 541 exists in the movement direction, there is a danger of the retractor 520 colliding with the organ 541 and the organ 541 being damaged. In this way, a support arm apparatus according to position control is not necessarily considered to be suitable to the use of holding the organ 541.

Meanwhile, as described above, in the present embodiment, force control is used as the control method of the support arm apparatus 500. With force control, it is possible to detect the force acting on the retractor 520 with a torque sensor provided in each of the joint units 511a to 511f, and control the operation of the arm unit 510 on the basis of the detected force acting on the retractor 520. For example, in a case in which a force equal to or greater than a certain threshold value is acting on the retractor 520, the arm unit 510 can be made to operate so as to release that force (in other words, cancel out the force acting on the retractor 520). In a case in which a force equal to or greater than a certain threshold value is acting on the retractor 520, it is conceivable that an unintended force is being imparted to the retractor 520 due to the position of the organ 541 changing or the retractor 520 contacting the organ 541. Thus, by conducting such control, a situation in which the organ 541 is damaged by the retractor 520 can be avoided.

In this way, the support arm apparatus 500 according to the present embodiment supports the retractor 520 while also controlling the operation of the retractor 520 by force control, thereby making it possible to hold the organ 541 more safely with the retractor 520.

Hereinafter, a configuration of a support arm apparatus 500 according to the present embodiment will be described in further detail.

(2. Configuration of Support Arm Apparatus)

(2-1. Overall Configuration)

Figure 2:
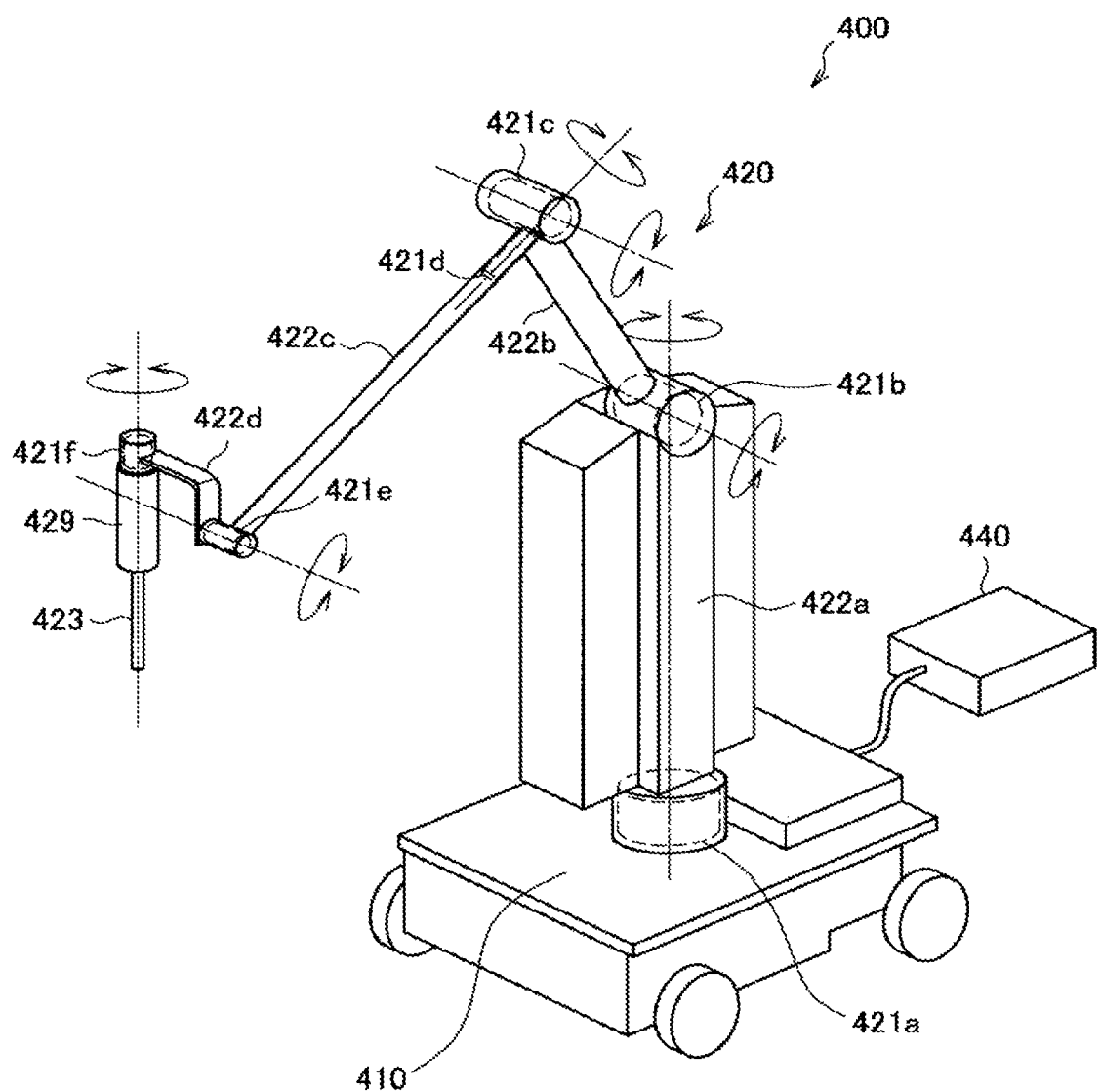
FIG. 2 is a diagram illustrating an overall configuration of a support arm apparatus according to the present embodiment.

An overall configuration of a support arm apparatus according to the present embodiment will be described with reference to FIG. 2. FIG. 2 is a diagram illustrating an overall configuration of a support arm apparatus according to the present embodiment.

Referring to FIG. 2, the support arm apparatus 400 is provided with a base unit 410, an arm unit 420, and a control device 440. The support arm apparatus 400 is expressed as a more specific configuration of the support arm apparatus 500 illustrated in FIG. 1 described earlier, and similarly to the support arm apparatus 500, is a medical support arm apparatus that uses a retractor to hold an organ of a patient during surgery.

The support arm apparatus 400 is equipped with a base unit 410, an arm unit 420, and a control device 430. Similarly to the support arm apparatus 510 illustrated in FIG. 8 described above, the support arm apparatus 400 is a medical support arm apparatus that may be applied favorably to procedures such as surgeries and examinations. However, the configuration of the support arm apparatus 400 according to the present embodiment is not limited to such an example. For example, a support arm apparatus 400 may be configured in which the base unit 410 is not provided, and the arm unit 420 is attached directly to the ceiling or a wall of the operating room. For example, in the case in which the arm unit 420 is attached to the ceiling, the support arm apparatus 400 is configured so that the arm unit 420 hangs down from the ceiling.

The arm unit 420 includes multiple joint units 421a, 421b, 421c, 421d, 421e, and 421f, multiple links 422a, 422b, 422c, and 422d rotatably joined to each other by the joint units 421a to 421e, a holding unit 429 rotatably provided on the front end of the arm unit 420 via the joint unit 421f, and a retractor 423 attached to the holding unit 429.

The links 422a to 422d are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Furthermore, the other end of the link 422c is joined to one end of the approximately L-shaped link 422d via the joint unit 421e, while the other end of the link 422d and the holding unit 429 that holds the retractor 423 are joined via the joint unit 421f. As described above, the arm shape extending from the base unit 410 is configured such that the base unit 410 serves as a support point, and the ends of the plurality of links 422a to 422d are connected with one another through the joint units 421a to 421f.

The retractor 423 corresponds to the retractor 520 illustrated in FIG. 1 described earlier, and is a tool that holds an organ of a patient during surgery. When performing surgery, the position and the orientation of the arm unit 420 and the retractor 423 are controlled by the support arm apparatus 400 so that the organ of the patient is held by the retractor 423. By having the organ of the patient be held appropriately by the retractor 423, a work space around the operating site on which the surgeon is to perform a process is secured.

Note that in FIG. 1, for the sake of simplicity, the specific shape of the retractor 423 is omitted from illustration, but in actuality, a suitable retractor 423 may be selected and used from among various types of retractors 520 having a variety of shapes, in accordance with the surgical technique and the object to be held. As described earlier with reference to FIG. 1, during endoscopic surgery or abdominal surgery, the retractor 423 may be inserted into the body cavity of the patient, and hold an organ inside the body cavity. Alternatively, during abdominal surgery, the retractor 423 may hold the body wall opened at an abdominal incision so as to spread the body wall outward. The holding unit 429 may be configured so that the retractor 423 is detachable, and an appropriate type of retractor 423 is attached to the holding unit 429 in accordance with the surgical technique and the object to be held.

FIGS. 3 to 6 illustrate examples of the retractor 423. FIGS. 3 to 6 are diagrams illustrating examples of the retractor 423 supported by the support arm apparatus 400.

Figure 3:
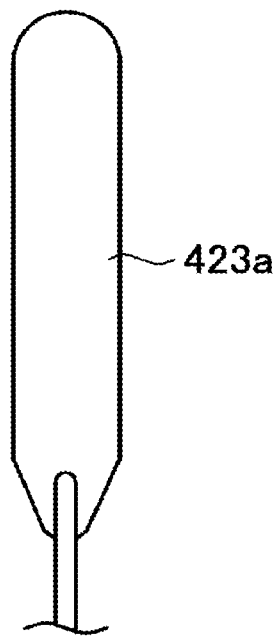
FIG. 3 is a diagram illustrating an example of a retractor supported by a support arm apparatus.

As illustrated in FIG. 3, the retractor 423 may be a paddle-shaped retractor 423a. With the paddle-shaped retractor 423a, the paddle-shaped part can be pressed against an organ, thereby moving the organ in a certain direction.

Figure 4:
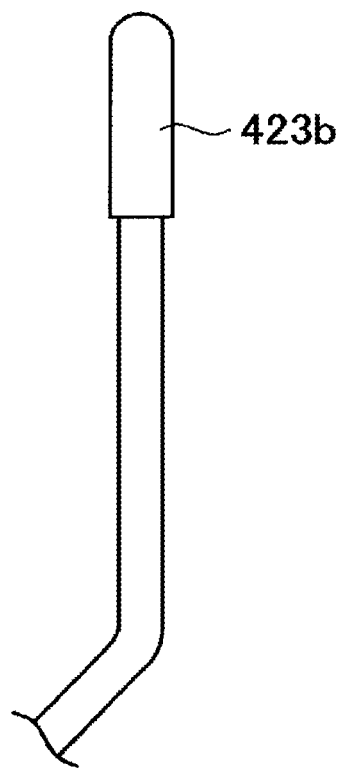
FIG. 4 is a diagram illustrating an example of a retractor supported by a support arm apparatus.

Also, as illustrated in FIG. 4, the retractor 423 may be a rod-shaped retractor 423b. With the rod-shaped retractor 423b, the tip of the rod-shaped part can be pressed against an organ, or the tip of the rod-shaped part can seize and stretch an organ, thereby moving the organ in a certain direction.

Figure 5:
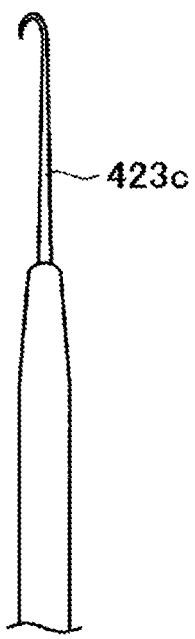
FIG. 5 is a diagram illustrating an example of a retractor supported by a support arm apparatus.

Also, as illustrated in FIG. 5, the retractor 423 may be a claw-shaped retractor 423c. With the claw-shaped retractor 423c, the claw-shaped part can seize and stretch an organ, thereby moving the organ in a certain direction.

Figure 6:
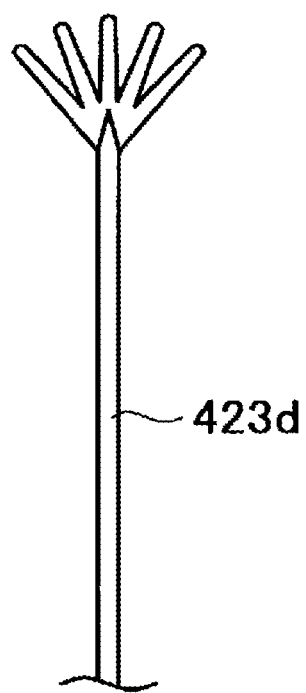
FIG. 6 is a diagram illustrating an example of a retractor supported by a support arm apparatus.

Also, as illustrated in FIG. 6, the retractor 423 may be a retractor 423d having a fan-shaped paddle part made up of multiple flat parts. With the retractor 423d having a fan-shaped paddle part, the paddle part can be pressed against an organ, thereby moving the organ in a certain direction.

Note that the illustrations in FIGS. 3 to 6 are merely examples, and any known type of retractor can be used as the retractor 423.

Returning to FIG. 2, the description of the configuration of the support arm apparatus 400 will continue.

The joint units 421a to 421f are each provided with an actuator 430 illustrated in FIG. 7 to be described later, and the joint units 421a to 421f are configured to be rotatable about a certain rotary shaft according to the driving of the actuator 430. The driving of the actuator 430 is controlled by the control device 440. By respectively controlling the driving of the actuator 430 in each of the joint units 421a to 421f, driving of the arm unit 420 is controlled so as to extend or contract (fold up) the arm unit 420, for example.

Note that in the example illustrated in the drawing, the support arm apparatus 400 includes six joint units 421a to 421f, and six degrees of freedom are realized with respect to the driving of the arm unit 420. By configuring the arm unit 420 to have six degrees of freedom, the retractor 423 can be moved freely within the movable range of the arm unit 420. With this arrangement, it becomes possible to make the retractor 423 approach the patient from various angles, and the degree of freedom when holding an organ of the patient with the retractor 423 is improved.

However, the configuration of the arm unit 420 is not limited to the example illustrated in the drawing, and factors such as the numbers of the joint units 421a to 421f and the links 422a to 422d, their arrangement, and the directions of the drive shafts of the joint units 421a to 421f, may be set appropriately so that the arm unit 420 has the desired degrees of freedom. However, in consideration of freedom in the position and the orientation of the retractor 423, the arm unit 420 preferably may be configured to have six or more degrees of freedom.

The control device 440 is made up of a processor, such as a central processing unit (CPU) or a digital signal processor (DSP), for example, or a microcontroller with these processors installed onboard. By executing signal processing according to a certain program, the control device 430 controls the driving of the support arm apparatus 400.

In the present embodiment, force control is used as the control method of the support arm apparatus 400. With force control, the force acting on the arm unit 420 and the retractor 423 is detected by a torque sensor of an actuator 430 provided in each of the joint units 421a to 421f. On the basis of the detected force, a generated torque that needs to be generated by the actuator 430 provided in each of the joint units 421a to 421f in order for the arm unit 420 to conduct a desired operation is computed, and this computed generated torque is used as a control value to control the operation of the arm unit 420.

With force control, the driving of the actuator 430 may be controlled by the control device 440 and the operation of the arm unit 420 may be controlled in response to an operation in which the surgeon touches the arm unit 420 directly to move the arm unit 420, for example, so that the arm unit 420 moves in the direction of a force imparted to the arm unit 420 (in other words, so that the arm unit 420 tracks the action by the surgeon). In this way, by using force control, the surgeon is able to move the arm unit 420 while touching the arm unit 420 directly, thereby making easier and more intuitive operations possible. Note that a specific control method of the support arm apparatus 400 by force control will be described in detail in (3. Control method of support arm apparatus) below.

Note that in the example illustrated in the drawing, the control device 440 is connected to the base unit 410 via a cable, but a component such as a control board having functions similar to the control device 440 may also be provided internally inside the base unit 410.

The above thus describes a schematic configuration of the support arm apparatus 400 according to the present embodiment with reference to FIG. 2.

(2-2. Configuration of Actuator)

A configuration of the actuator provided in each of the joint units 421a to 421f of the support arm apparatus 400 illustrated in FIG. 2 will be described with reference to FIG. 7. FIG. 7 is a cross-section diagram illustrating an exemplary configuration of an actuator provided in the joint units 421a to 421f of the support arm apparatus 400 illustrated in FIG. 2. FIG. 3 illustrates a cross-section view of the actuator according to the present embodiment in the case of cutting on a plane that goes through the rotating shaft.

Figure 7:
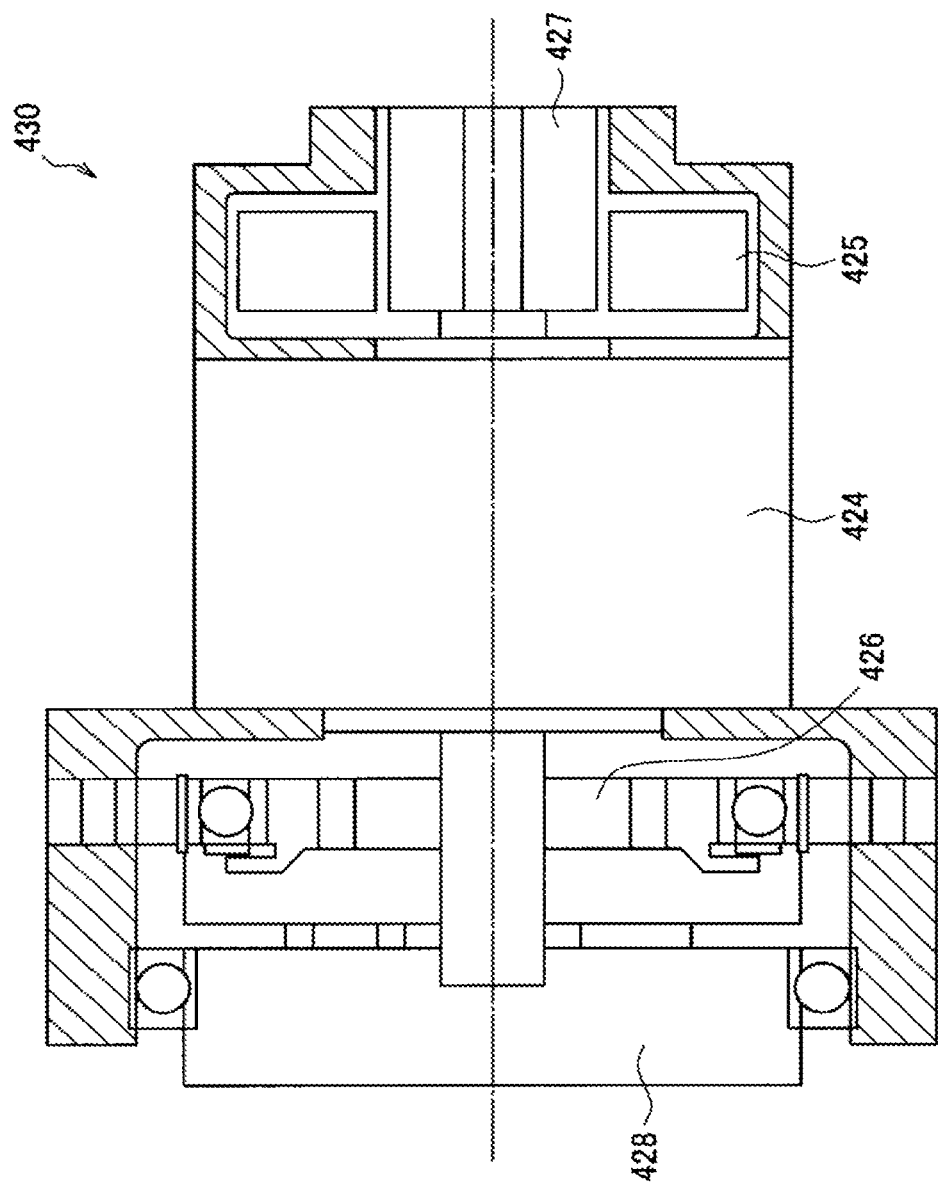
FIG. 7 is a cross-section diagram illustrating an exemplary configuration of an actuator provided in a joint unit of the support arm apparatus illustrated in FIG. 2.

Referring to FIG. 7, the actuator 430 according to the present embodiment is made up of a motor 424, a motor driver 425, a reduction gear 426, an encoder 427, and a torque sensor 428. The actuator 430 is an actuator corresponding to force control. In the actuator 430, the rotation of the motor 424 is reduced by the reduction gear 426 at a certain reduction ratio, and transmitted to other downstream members via an output shaft. As a result, the other members are driven.

The motor 424 is a driving mechanism that, in a case of being given a certain command value (current command value), causes a rotating shaft to rotate at a rotational velocity corresponding to the command value, and thereby produces driving force. For the motor 424, a brushless motor is used, for example. However, the present embodiment is not limited to such an example, and any of various known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to the torque command value $\tau$ illustrated in FIG. 10 described later.

The reduction gear 426 is joined to the rotating shaft (drive shaft) of the motor 424. The reduction gear 426 reduces by a certain reduction ratio the rotational velocity of the rotating shaft of the joined motor 424 (in other words, the rotational velocity of the input shaft), and transmits to the output shaft. In the present embodiment, the configuration of the reduction gear 426 is not limited to a specific configuration, and any of various known types of reduction gears may be used as the reduction gear 426. However, for the reduction gear 426, it is preferable to use one capable of accurately setting the reduction ratio, such as a Harmonic Drive (registered trademark), for example. In addition, the reduction ratio of the reduction gear 426 may be set appropriately according to the application of the actuator 430. For example, in the case of applying the actuator 430 to the joint units 421a to 421f of the support arm apparatus 400 as in the present embodiment, a reduction gear 426 having a reduction ratio of approximately 1:100 may be used favorably.

The encoder 427 detects the rotational angle of the input shaft (that is, the rotational angle of the rotating shaft of the motor 424). On the basis of the rotation rate of the input shaft detected by the encoder 427, and the reduction ratio of the reduction gear 426, information such as the rotational angle, the rotational angular velocity, and the rotational angular acceleration of the joint units 421a to 421f may be obtained. For the encoder 427, any of various known types of rotary encoders, such as a magnetic encoder or an optical encoder, for example, may be used. Note that in the illustrated example, the encoder 427 is provided only on the input shaft of the actuator 430, but an encoder for detecting the rotational angle of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside.

The above thus describes a configuration of the actuator 430 according to the present embodiment with reference to FIG. 7. In a case in which force control is conducted, in the support arm apparatus 400, the rotational angle of each of the joint units 421a to 421f and the torque acting on each of the joint units 421a to 421f are detected respectively by the encoder 427 and the torque sensor 428 provided in each actuator 430. At this point, the torque acting on each of the joint units 421a to 421f detected by the torque sensor 428 may also include force acting on the arm unit 420 and/or the retractor 423.

On the basis of the detected rotational angle and torque value, the torque that needs to be generated by the actuator 430 of each of the joint units 421a to 421f in order for the arm unit 420 to realize a desired operation is computed, and this torque is used as a control value to drive the actuator 430 of each the joint units 421a to 421f. A specific control method of the support arm apparatus 400 by force control will be described in detail in (3. Control method of support arm apparatus) below.

Note that the configuration illustrated in FIG. 7 merely illustrates one exemplary configuration of the actuator 430 according to the present embodiment, and the present embodiment is not limited to such an example. For the actuator 430, it is possible to use any of various known types of actuators typically used in various devices whose behavior is controlled by force control.

(3. Control Method of Support Arm Apparatus)

Figure 8:
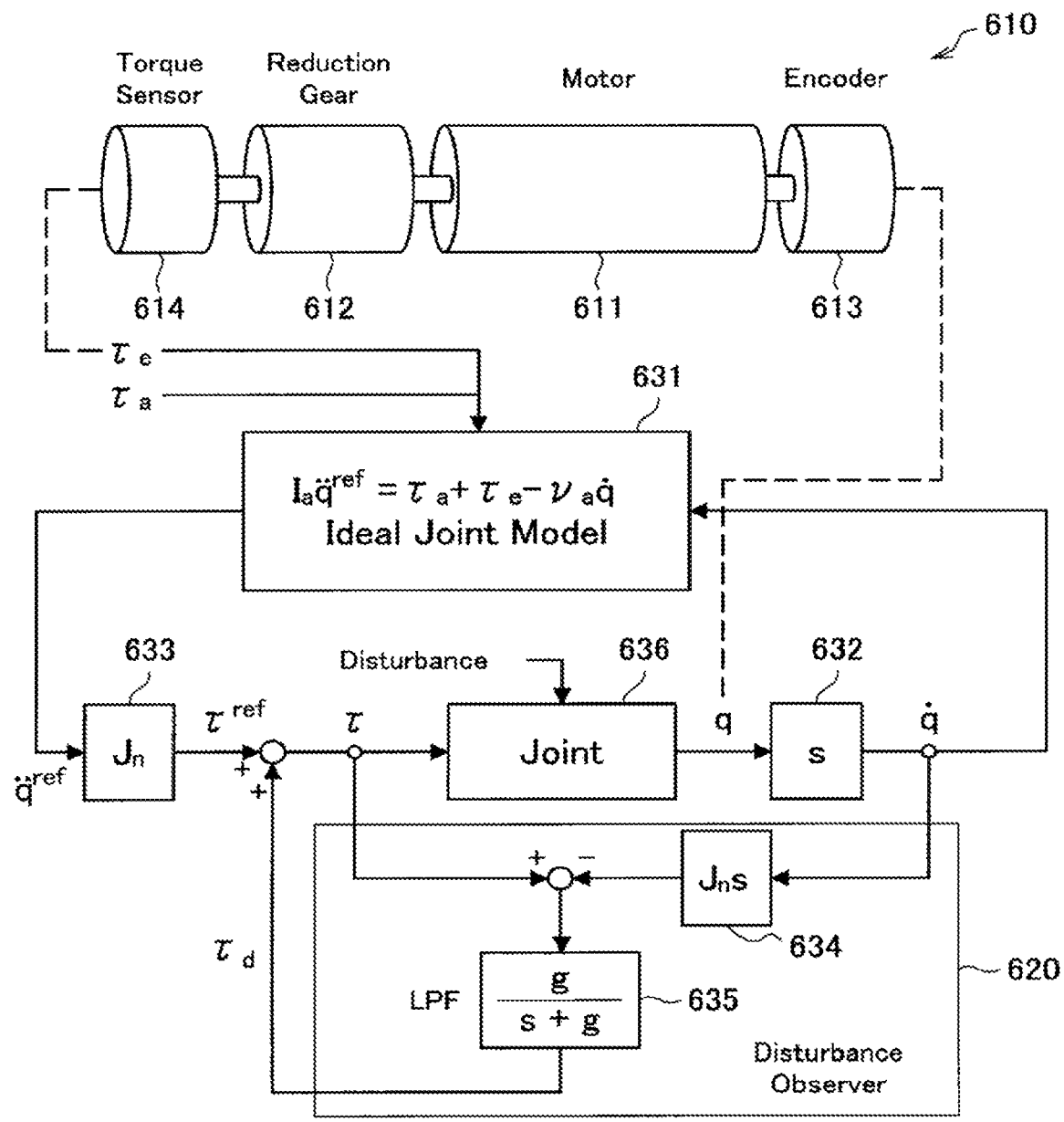
FIG. 8 is a block diagram illustrating a control method of a support arm apparatus according to the present embodiment.

A control method of the support arm apparatus 400 according to the present embodiment will be described with reference to FIG. 8. FIG. 8 is a block diagram illustrating a control method of the support arm apparatus 400 according to the present embodiment. FIG. 8 focuses on one actuator 430 constituting the arm unit 420 of the support arm apparatus 400, and illustrates a flow of processing when controlling the driving of that actuator 430 as a block diagram. By conducting similar processing with respect to each actuator 430 provided in each of the joint units 421a to 421f, the operation of the arm unit 420 is controlled.

Each block illustrated in FIG. 8 represents a conceptual simulation of a computing element that performs various computations related to driving control of the actuator 430. The processes in each of these blocks (computing element) may be realized by the control device 440 described earlier.

Note that the block diagram illustrated in FIG. 8 merely illustrates one example of processing in the case in which the actuator 430 is driven by force control, and the present embodiment is not limited to such an example. For the driving control method of the actuator 430, any of various known types of control methods typically used as a control method for force control may be used.

Before describing actual processing in detail while referring to the block diagram illustrated in FIG. 8, an overview of the control method illustrated in the block diagram will be described.

The motion of each actuator 430 of the support arm apparatus 400 is modeled by the equation of second-order lag motion expressed in Formula (1) below.

[Math. 1]

$$I_a \ddot{q}^{ref} = \tau_a + \tau_e - \nu_a \dot{q} \qquad (1)$$

Herein, q is the rotational angle of the actuator 430, $q^{ref}$ is a rotational angle target value of the actuator 430, $I_a$ is the inertial moment of the actuator 430, $\tau_a$ is the generated torque of the actuator 430, $\tau_e$ is the external torque acting on the actuator 430 from the outside, and $\nu_a$ is a viscous drag coefficient for the actuator 430. The above Formula (1) is a theoretical model expressing the motion of the actuator 430 in each of the joint units 421a to 421f.

With force control, the driving of the actuator 430 is controlled by using torque as the control quantity. In the case of causing the arm unit 420 to operate, the torque $\tau_a$ (generated torque $\tau_a$) to be generated by the actuator 430 in each of the joint units 421a to 421f in order to realize the desired operation may be computed. Note that since any of various existing methods may be used as the method of computing the generated torque $\tau_a$, a detailed description is reduced or omitted in this specification. For example, the generated torque $\tau_a$ may be computed by a method typically used in a control method called whole body cooperative control (a control method that controls driving of multiple driving units (actuators) cooperating with each other, and achieves a desired operation as a whole). For details regarding the method of computing the generated torque $\tau_a$ in whole body cooperative control, literature such as JP 2009-95959A and JP 2010-188471A, which are prior patent applications filed by the applicant, may be referenced.

Ideally, by applying the generated torque $\tau_a$ computed for each actuator 430 to Formula (1) above, a response obeying the theoretical model expressed in Formula (1) above should be realized in each actuator 430, or in other words, the desired operation should be realized in the arm unit 420.

However, in actuality, the influence of various disturbances causes error (modeling error) to occur between the actual motion in the actuator 430 and the theoretical model expressed in Formula (1) above in some cases. Modeling error may be divided roughly into error arising from mass properties, such as the mass, center of gravity, and inertia tensor of a multi-link structure (in other words, the arm unit 420 to be controlled), and error arising from factors such as friction and inertia internal to the actuator 430. Of these, the former modeling error arising from mass properties may be reduced comparatively easily during construction of the theoretical model by increasing the precision of computer-aided design (CAD) data and applying identification techniques.

On the other hand, the latter modeling error arising from factors such as friction and inertia internal to the actuator 430 is caused by phenomena which are difficult to model, such as friction in the reduction gear 426, for example. Accordingly, modeling error non-negligible modeling error may still remain during construction of the theoretical model. Additionally, there is also a possibility of error occurring between the values of the inertia $I_a$ and the viscous drag coefficient $\nu_a$ in Formula (1) above, and these values in the actual actuator 430. These difficult-to-model errors arising from factors such as friction and inertia internal to the actuator 430 may become disturbances in the driving control of the actuator 430. Thus, because of the influence of such disturbances, in actuality, cases occur in which the motion of the actuator does not respond exactly like the theoretical model expressed in Formula (1) above, or in other words, the desired operation is not realized.

Accordingly, in the present embodiment, an active control system is added to the actuator 430 to thereby correct the response of the actuator 430 so as to perform ideal response obeying the theoretical model expressed in Formula (1) above. Note that controlling the driving of the actuator 430 so that the actuators 430 of the support arm apparatus 400 (that is, the joint units 421a to 421f) perform ideal response as expressed in Formula (1) above in this way is designated ideal joint control in the present embodiment. The block diagram illustrated in FIG. 8 is an illustration of a series of processes for such ideal joint control with respect to the actuator 430 in one joint unit among the joint units 421a to 421f of the support arm apparatus 400.

Hereinafter, a process according to the driving control of the actuator 430 will be described in detail with reference to FIG. 8. Referring to FIG. 8, the actuator 610 illustrates a simulation of the functions of the actuator 430 illustrated in FIG. 7, for example. In FIG. 8, a motor 611, a reduction gear 612, an encoder 613, and a torque sensor 614 are illustrated as component members of the actuator 610. These respectively correspond to the motor 424, the reduction gear 426, the encoder 427, and the torque sensor 428 illustrated in FIG. 7.

The computing element 631 is a computing element that perform computation in accordance with the ideal joint model of the actuator 610 (that is, joint units 421a to 421f) expressed in Formula (1) above. The computing element 631 is able to take the generated torque $\tau_a$, the external torque $\tau_e$, and the rotational angular velocity (the first derivative of the rotational angle q) as input, and output the rotational angular acceleration target value (the second derivative of the rotational angle target value $q^{ref}$) expressed on the left side of Formula (1) above.

Herein, The actuator 610 performing response obeying the ideal model expressed in Formula (1) above means nothing other than that when the right side of Formula (1) above is given, the rotational angular acceleration on the left side is achieved. However, as above, ideal response obeying Formula (1) above actually is not produced sometimes, due to the influence of disturbances. Accordingly, in the present embodiment, a disturbance observer 620 is introduced. A process is conducted in which a disturbance estimate value $\tau_d$, which is an estimate value of the torque arising from a disturbance by the disturbance observer 620, is computed, and the disturbance estimate value $\tau_d$ is used to correct the calculation result by the computing element 631.

Hereinafter, specific processes will be described in order. First, the generated torque $\tau_a$ for realizing a desired operation computed on the basis of a method used in typical force control, and the external torque $\tau_e$ detected by the torque sensor 614, are input into the computing element 631. Meanwhile, by inputting the rotational angle q of the actuator 610 detected by the encoder 613 into a computing element 632 that performs differential computations, the rotational angular velocity (the first derivative of the rotational angle q) of the actuator 610 is computed. By inputting the rotational angular velocity computed by the computing element 632, in addition to the generated torque $\tau_a$ and the external torque $\tau_e$ above, into the computing element 631, the rotational angular acceleration target value (the second derivative of $q^{ref}$) is computed by the computing element 631. The computed rotational angular acceleration target value is input into a computing element 633.

The computing element 633 is a computing element that computes the torque generated in the actuator 610, on the basis of the rotational angular acceleration of the actuator 610. In the present embodiment, specifically, the computing element 633 calculates a torque target value $\tau^{ref}$ by multiplying the rotational angular acceleration target value computed by the computing element 631 by the nominal inertia $J_n$ of the actuator 610. In ideal response, the actuator 610 is driven so as to output the torque target value $\tau^{ref}$, and thus the desired operation should be realized, but as described earlier, the influence of disturbances and the like is produced in the actual response in some cases. Consequently, in the present embodiment, the torque target value $\tau^{ref}$ is corrected using the disturbance estimate value $\tau_d$ computed by the disturbance observer 620.

The configuration of the disturbance observer 620 will be described. The disturbance observer 620 computes the disturbance estimate value $\tau_d$, on the basis of the torque command value $\tau$ and the rotational angular velocity computed from the rotational angle q of the actuator 610 detected by the encoder 613. Herein, the torque command value $\tau$ is the command value ultimately given to the actuator 610 after the influence of disturbances is corrected. In other words, in the control system illustrated in FIG. 8, the actuator 610 is driven so as to output the torque command value $\tau$. For example, in the case in which the disturbance estimate value $\tau_d$ is approximately zero, the torque command value $\tau$ becomes a value approximately equal to the torque target value $\tau^{ref}$.

Specifically, the disturbance observer 620 is made up of a computing element 634 and a computing element 635. The computing element 634 is a computing element that computes the torque generated in the actuator 610, on the basis of the rotational angular velocity of the actuator 610. Input into the computing element 634 is the rotational angular velocity computed by the computing element 632 on the basis of the rotational angle q detected by the encoder 613. The computing element 634 performs computations expressed by a transfer function $J_n s$ on the input rotational angular velocity, or in other words, finds the rotational angular acceleration by taking the derivative of the rotational angular velocity, and additionally multiplies the computed rotational angular acceleration by the nominal inertia $J_n$, and thereby computes an estimate value of the torque (torque estimate value) actually acting on the actuator 610.

Inside the disturbance observer 620, by taking the difference between the torque estimate value and the torque command value $\tau$, the value of the torque due to disturbances, that is, the disturbance estimate value $\tau_d$, is estimated. Specifically, the disturbance estimate value $\tau_d$ is the difference between the torque command value $\tau$ from the control in the previous step, and the torque estimate value from the control in the current step. Since the torque estimate value computed by the computing element 634 is based on an actual measured value, and the torque command value $\tau$ computed by the computing element 633 is based on an ideal theoretical model of the actuator 610 computed by the computing element 631, by taking the difference between the two, the influence of disturbances not taken into account by the theoretical model above can be estimated.

The computing element 635 is a computing element provided to prevent divergence of the system, and includes the function of a low-pass filter (LPF). The computing element 635 performs the computations expressed by the transfer function g/(s+g) to thereby output only the low-frequency component with respect to an input value, and stabilize the system. The difference value between the torque estimate value and the torque target value $\tau^{ref}$ computed by the computing element 634 is input into the computing element 635, and the low-frequency component thereof is computed as the disturbance estimate value $\tau_d$.

After the disturbance estimate value $\tau_d$ is computed by the disturbance observer 620, the disturbance estimate value $\tau_d$ is added to the theoretical value, that is, the torque target value $\tau^{ref}$ to thereby compute the torque value to ultimately generate in the actuator 610, that is, the torque command value $\tau$. The computed torque command value $\tau$ is input into a block 636 representing a joint unit. The block 636 expresses a simulation of the joint units 421a to 421f (in other words, the actuator 610). In the block 636, the actuator 610 is driven on the basis of the torque command value $\tau$. Specifically, in the block 636, by converting the torque command value $\tau$ into a corresponding current value (current command value), and applying this current command value to the motor 611, the actuator 610 is driven so as to output torque corresponding to the torque command value $\tau$.

By executing the processing described above respectively for the actuator 430 of each of the joint units 421a to 421f constituting the arm unit 420 of the support arm apparatus 400, the operation of the arm unit 420 may be controlled so that the arm unit 420 conducts a desired operation.

The above thus describes a control method of the support arm apparatus 400 according to the present embodiment with reference to FIG. 8.

Herein, with force control, when computing the generated torque $\tau_a$, by computing the generated torque $\tau_a$ while imposing a variety of purposes of motion and constraint conditions, a wide array of operations can be realized in the arm unit 420. The purpose of motion refers to a desired operation to be conducted by the arm unit 420, while a constraint condition refers to a restriction imposed on the operation of the arm unit 420 when the arm unit 420 operates, such as a restriction on position, speed, or force.

For example, as illustrated in FIG. 8, with force control, the force acting on each of the joint units 421a to 421f, or in other words, the force acting on the arm unit 420 and the retractor 423 (force imparted to an external object that the arm unit 420 and the retractor 423 are contacting, and force imparted to the arm unit 420 and the retractor 423 from outside) is monitored continually by the torque sensor 428 of the actuator 430 provided in each of the joint units 421a to 421f For example, by utilizing the above to set a purpose of motion and a constraint condition appropriately, the driving of the arm unit 420 may be controlled so that the force acting on the retractor 423 does not exceed a certain threshold value.

By conducting such control, for example, in a case in which a force greater than the certain threshold value acts on the retractor 423, the arm unit 420 can be made to operate so as to release that force (in other words, cancel out the force acting on the retractor 423). Consequently, in a case of contacting an organ while moving the retractor 423 inside the body cavity, or in a case in which an organ moves unintentionally while the organ is being held by the retractor 423, it is possible to prevent a force equal to or greater than a certain magnitude from being imparted to the organ by the retractor 423, and a situation in which the organ is damaged can be avoided.

Also, when detecting the force acting on the retractor 423, the force acting on the retractor 423 due to the weight of a held organ may be detected, and the driving of the arm unit 420 may be controlled to cancel out the detected force acting on the retractor 423 due to the weight of the organ. By conducting such control, in a case in which the surgeon moves the arm unit 420 in a state in which an organ is being held by the retractor 423, the surgeon is able to move the arm unit 420 with less force, without feeling the weight of the organ.

Also, the operation of the arm unit 420 may be controlled so that what is called a power assist operation is realized. A power assist operation is one type of control typically used widely among various types of devices driven by force control. In a power assist operation, the driving of the arm unit 420 is controlled to support the movement of the arm unit 420 in the direction of a force imparted from outside in accordance with an operation performed by the surgeon. By conducting a power assist operation, in a case in which the surgeon moves the arm unit 420 manually, the surgeon is able to move the arm unit 420 with less force, as if moving the arm unit 420 in a weightless environment, and higher operability is realized.

Otherwise, any of various types of controls typically used in force control may be applied to the driving control of the support arm apparatus 400.

(4. Exemplary Application of Support Arm Apparatus to Surgery)

Examples of applying the support arm apparatus 400 according to the present embodiment to surgery will be described specifically.

(4-1. Exemplary Application to Abdominal Surgery)

Figure 9:
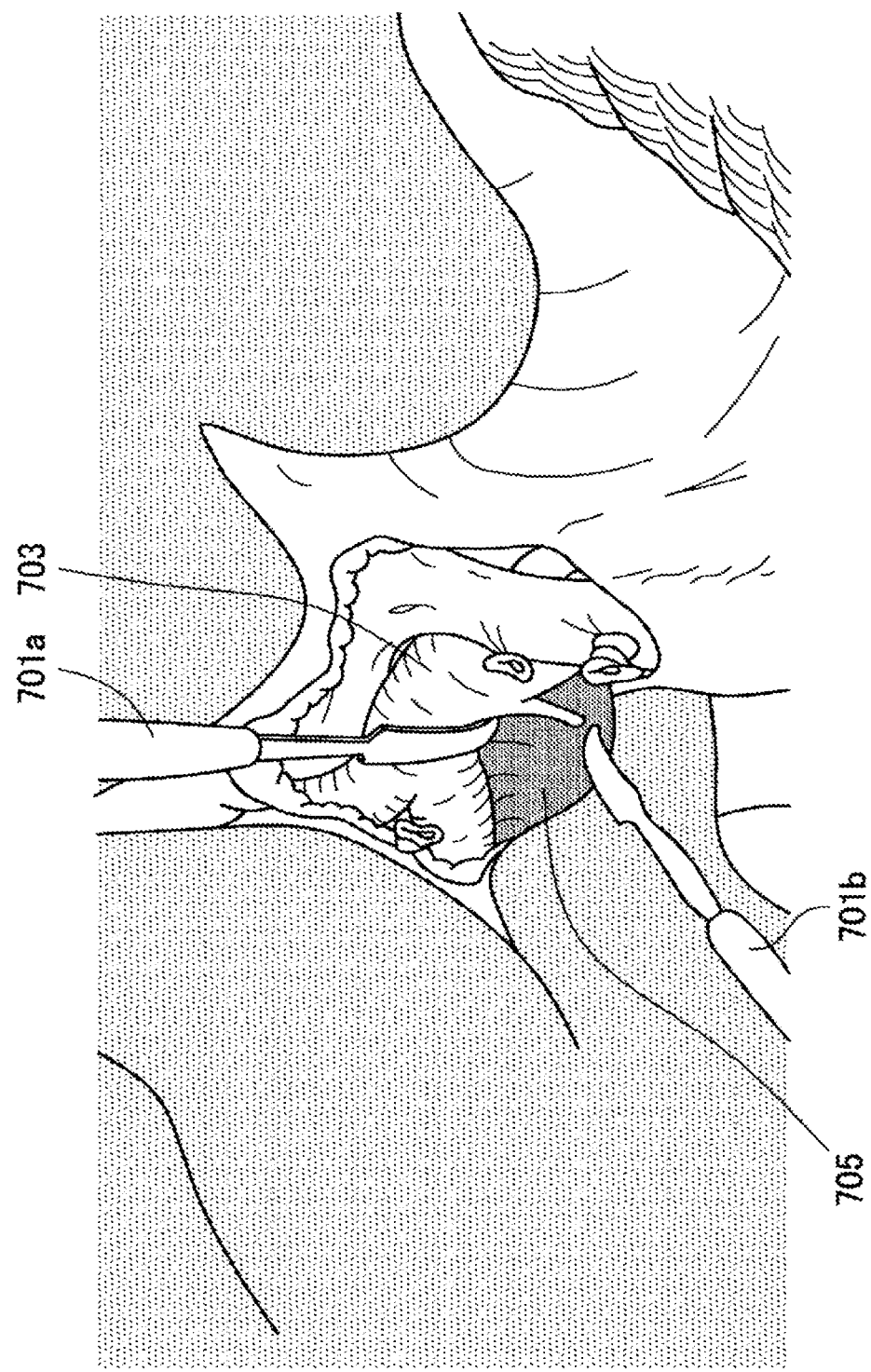
FIG. 9 is a diagram illustrating an example of holding an organ with a retractor during abdominal surgery.

FIG. 9 is a diagram illustrating an example of holding an organ with a retractor during abdominal surgery. As an example, FIG. 9 illustrates a state in which a right portal branch vein 703 and part of the tissue of the liver are held respectively by two retractors 701a and 701b having curved paddle-shaped tips, and part of a caudate lobe protrusion 705 of the liver is exposed. In this way, during abdominal surgery, the retractors 701a and 701b are inserted into the body cavity of a patient from an abdominal incision, and hold organs inside the body cavity. In this exemplary application, the retractors 701a and 701b may be supported respectively by two support arm apparatuses 400.

(4-2. Exemplary Application to Endoscopic Surgery)

Figure 10:
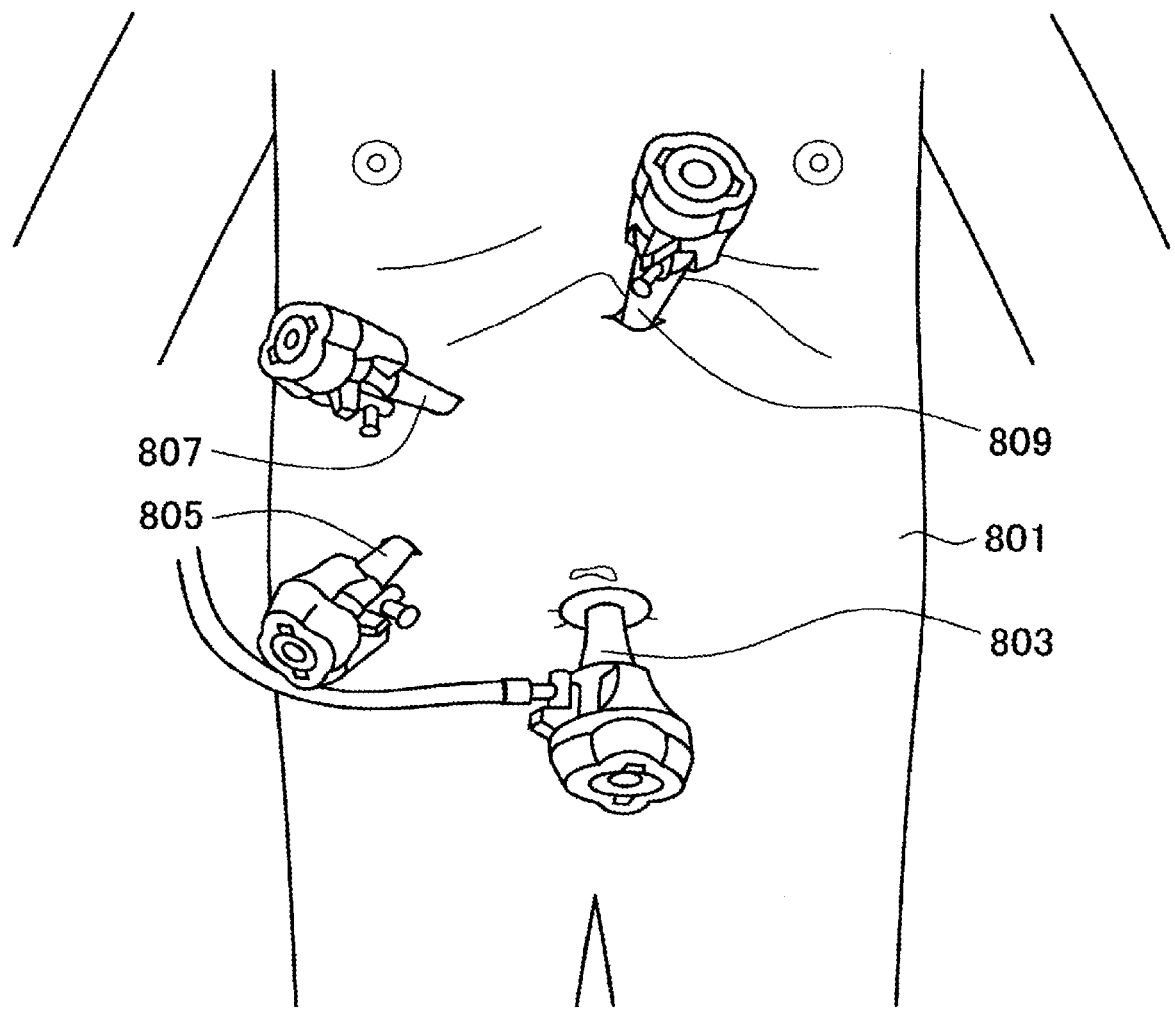
FIG. 10 is a diagram that schematically illustrates the insertion positions of an endoscope, forceps, and a retractor into a patient during endoscopic surgery.
Figure 11:
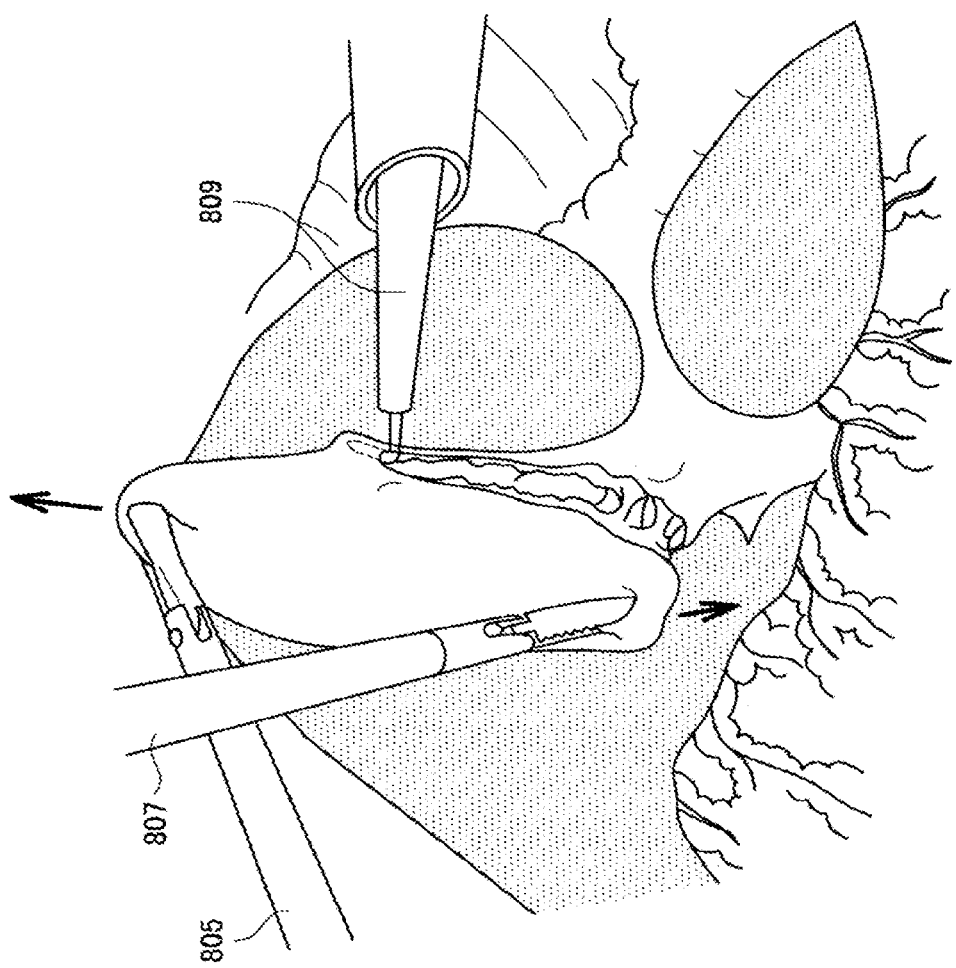
FIG. 11 is a diagram illustrating an example of holding an organ inside a body cavity of a patient with the forceps and retractor illustrated in FIG. 10.

FIG. 10 is a diagram that schematically illustrates the insertion positions of an endoscope, forceps, and a retractor into a patient during endoscopic surgery. FIG. 11 is a diagram illustrating an example of holding an organ inside a body cavity of a patient with the forceps and retractor illustrated in FIG. 10.

As illustrated in FIG. 10, in endoscopic surgery, several small insertion openings are made in the body of a patient 801, and from these insertion openings, various medical tools such as an endoscope 803, forceps 805 and 807, and a retractor 809 are inserted. The state of the operating site inside the body cavity is imaged by the endoscope 803, and displayed on a display device installed inside the operating room. The surgeon operates treatment tools such as the forceps 805 and 807 as well as the retractor 809 inserted from the insertion openings and performs various treatments on the operating site, while looking at an image of the operating site displayed on the display device.

As an example, FIG. 11 illustrates a state in which, inside the body cavity of a patient, the serosa of the gallbladder is seized by the retractor 809 having a claw-shaped tip similar to the retractor 423c illustrated in FIG. 5, while in addition, both ends of the gallbladder fundus are gripped by the forceps 805 and 807. Note that for the sake of simplicity, in FIG. 9, the endoscope 803 is omitted from illustration. In this exemplary application, the retractor 809 may be supported by the support arm apparatus 400.

The above thus specifically describes examples of applying the support arm apparatus 400 according to the present embodiment to surgery. As described above, in these exemplary applications, the retractors 701a, 701b, and 809 that hold organs of a patient during surgery may be supported by the support arm apparatus 400. Consequently, compared to the case in which the support of organs is performed manually like in the past, the burden on the physician (assistant) who holds the organs can be reduced, and in addition, it becomes possible to hold organs more stably. Also, as described above, in the support arm apparatus 400, since the driving of the arm unit 420 is controlled by force control, a situation in which surrounding organs are damaged by the retractors 701a, 701b, and 809 during surgery may be prevented favorably. In addition, the arm unit 420 can also be made to conduct operations that further improve operability for the surgeon who operates the arm unit 420 to hold organs, such as a power assist operation, for example.

(5. Modification)

A modification of the embodiment described above will be described. In the embodiment described above, the force acting on the retractor 423 is detected on the basis of a detection value of the torque sensor 428 of the actuator 430 in each of the joint units 421a to 421f. On the other hand, in the present modification, the retractor 423 is also provided with a sensor, and the force acting on the retractor 423 may be detected on the additional basis of a detection value from this sensor.

Note that the present modification corresponds to a change of the configuration of the retractor 423 in the support arm apparatus 400 according to the embodiment described above, and other items, such as the configuration and control method of the support arm apparatus 400, may be similar to the embodiment described above. Consequently, in the following description of the present modification, the items that differ from the foregoing embodiment will be described primarily, whereas detailed description of duplicate items will be reduced or omitted.

Figure 12:
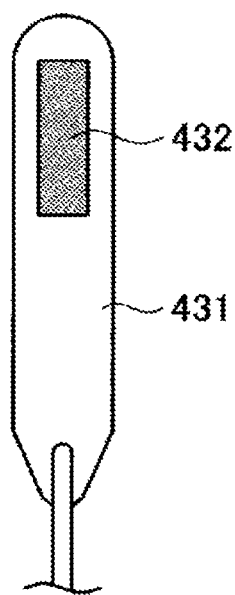
FIG. 12 is a diagram illustrating an example of a retractor according to a modification.

FIG. 12 is a diagram illustrating an example of a retractor according to the present modification. As illustrated in FIG. 12, in the present modification, a force sensor 432 is provided on the part where a retractor 431 contacts an organ. As an example, FIG. 12 illustrates a configuration in which the force sensor 432 is provided on a paddle-shaped retractor 431 similar to the retractor 423a illustrated in FIG. 3, but even in the case of using a retractor having another shape, the force sensor 432 similarly may be provided on the part that contacts an organ. In the present modification, the retractor 431 provided with the force sensor 432 as illustrated in FIG. 12 is supported by the support arm apparatus 400 illustrated in FIG. 2, and an organ is held by the retractor 431.

The force sensor 432 is a pressure sensor that detects the force pressing against the force sensor 432, for example, and by having the retractor 431 hold an organ so that the force sensor 432 contacts the organ, the contact pressure due to the organ may be detected by the force sensor 432. Alternatively, the force sensor 432 may be a strain sensor that detects stress corresponding to an amount of deformation of the retractor 431 to which the force sensor 432 is attached, for example.

In the present modification, when detecting the force acting on the retractor 431 to control the operation of the arm unit 420, the detection value of the force sensor 432 is used in addition to the detection value from the torque sensor 428 of the actuator 430 in each of the joint units 421a to 421f. By using the detection value of the force sensor 432 provided on the retractor 431, it becomes possible to detect the force acting on the retractor 431 more accurately, and by appropriately controlling the driving of the arm unit 420 using the detected force acting on the retractor 431, the danger of an organ being damaged by the retractor 431 can be lowered even further.

Also, in the present modification, the detection value of the force sensor 432 may also be used to detect slippage of an organ with respect to the retractor 431. As the method for detecting slippage, any of various known methods may be used. Herein, as an example, the method described in JP 2009-34744A submitted previously by the applicant will be described.

Figure 13:
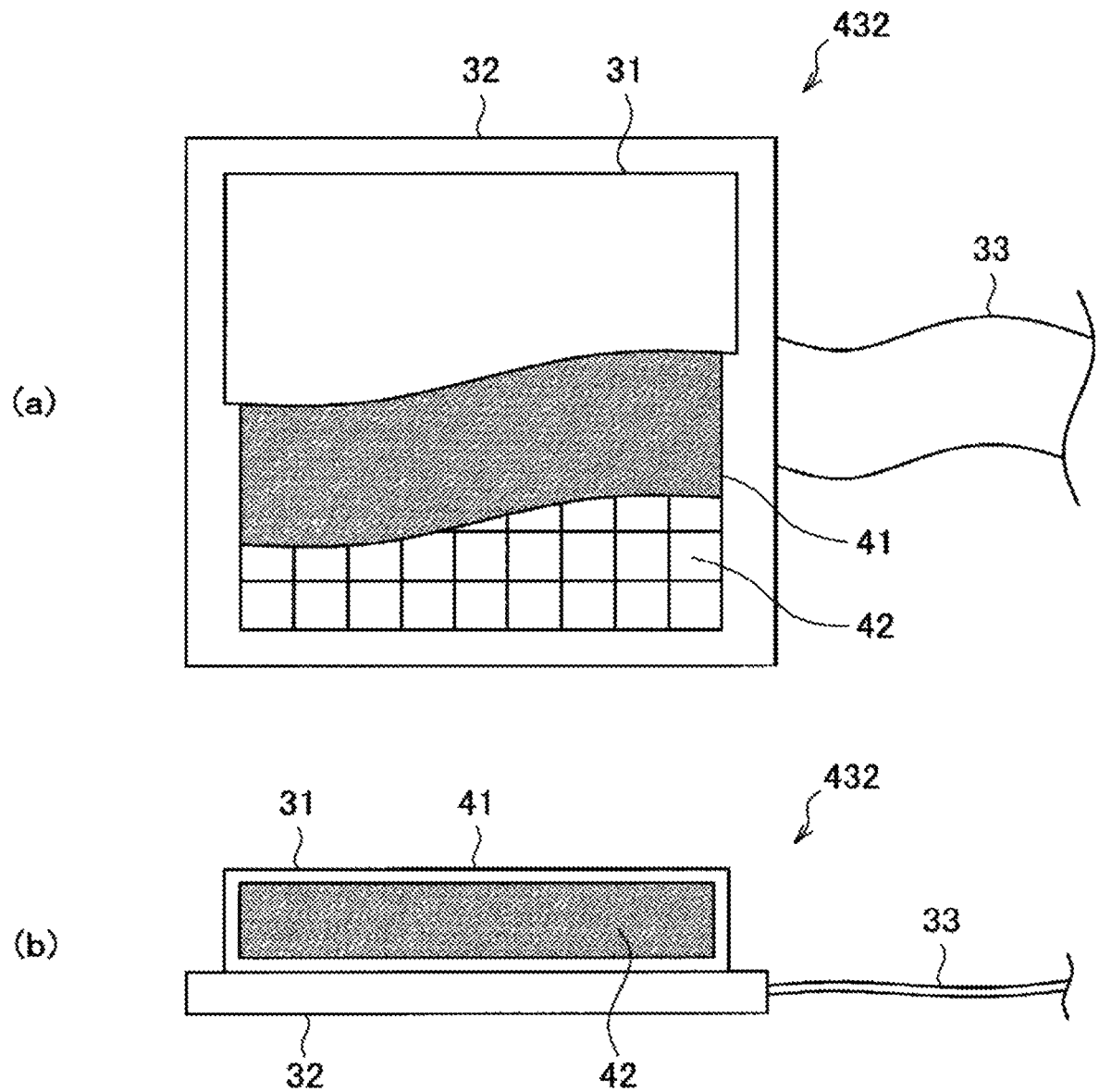
FIG. 13 is a diagram illustrating an exemplary configuration of a force sensor used to detect slippage.

In the method described in the above literature, a pressure sensor having the configuration illustrated in FIG. 13 is used as the force sensor 432. FIG. 13 is a diagram illustrating an exemplary configuration of the force sensor 432 used to detect slippage.

In FIG. 13, a top view ((a)) and a side cross-sectional view ((b)) of the force sensor 432 are illustrated. However, in the top view, to show the internal configuration of the force sensor 432, a state in which the respective layers constituting the force sensor 432 are made transparent in a stepwise manner is illustrated.

Referring to FIG. 13, the force sensor 432 primarily is made up of an input unit 31, which is the part that deforms and detects pressure in response to the contact of an object, a fixed unit 32 that supports the input unit 31, and an external connection unit 33 that outputs a detection result by the force sensor 432 to the outside (for example, the control device 440 illustrated in FIG. 2). Additionally, the input unit 31 primarily is made up of a pressure detection unit 42 and a deformation unit 41 laminated in that order.

The deformation unit 41 is made of a viscoelastic material having viscoelastic properties (a viscoelastic body) such as silicone gel material, for example, and is easily deformable in response to a load from the outside. The pressure detection unit 42 is made up of a capacitive pressure sensor or the like that detects pressure by utilizing electrostatic capacitance, for example.

If an organ makes contact with the detection surface of the force sensor 432, the deformation unit 41 deforms due to the contact, and a pressure corresponding to the deformation of the deformation unit 41 is detected by the pressure detection unit 42. At this point, the pressure detection unit 42 is able to detect the pressure as a distribution of force on the surface, but since stress variance is produced by the deformation of the deformation unit 41, and the pressure is diffused with respect to the internal pressure detection unit 42, sensing performance equal to or greater than the spatial resolution of a capacitive pressure sensor can be obtained.

Information about the surface distribution of force detected by the pressure detection unit 42 is transmitted via the external connection unit 33 to the control device 440 of the support arm apparatus 400 illustrated in FIG. 2, for example. The control device 440 computes a pressure center position on the basis of the surface distribution of force detected by the pressure detection unit 42, and by monitoring the amount of change over time in the pressure center position, the control device 440 is able to detect slippage of the organ with respect to the force sensor 432 (that is, with respect to the retractor 431) as well as the amount of slippage.

In the present modification, in a case in which the slippage of an organ with respect to the retractor 431 is detected, the operation of the support arm apparatus 400 may be controlled to conduct operation by which the organ may continue to be held. Alternatively, in a case in which the slippage amount of an organ with respect to the retractor 431 is detected, and the slippage amount is greater than a certain threshold value, the operation of the arm unit 420 may be controlled to conduct operation by which the organ may continue to be held.

For example, in a case in which the slippage of an organ with respect to the retractor 431 is detected, the support arm apparatus 400 issues a warning to the surgeon. The warning may be conveyed to the surgeon aurally with sound, or may be conveyed to the surgeon visually with light. In this case, the support arm apparatus 400 may be suitably provided with a sound output device such as a speaker or a display device such as an indicator light for issuing the warning. The surgeon receiving the warning is able to operate the arm unit 420 appropriately so that the organ continues to be held securely by the retractor 431.

Alternatively, in a case in which the slippage of an organ with respect to the retractor 431 is detected, the support arm apparatus 400 may cause the arm unit 420 to operate automatically so that the organ continues to be held securely. For example, if the organ is held by being pressed against another organ by the retractor 431, in a case in which the slippage of the organ with respect to the retractor 431 is detected, the support arm apparatus 400 can cause the arm unit 420 to operate so that the organ is pressed further by the retractor 431.

Note that the detection of the slippage of an organ with respect to the retractor 431 does not necessarily require a detection value from the force sensor 432 provided in the retractor 431. For example, vibrations which may be produced in the retractor 431 and the arm unit 420 due to slippage can also be detected on the basis of a detection value from the torque sensor 428 of the actuator 430 in each of the joint units 421a to 421f. Even in this case, on the basis of the slippage of an organ with respect to the retractor 431 detected on the basis of a detection value from the torque sensor 428, the support arm apparatus 400 may be controlled appropriately to perform various operations by which the organ may continue to be held.

(6. Supplement)

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A medical support arm apparatus, including:
an arm unit whose driving is controlled by force control; and
a retractor, provided on a front end of the arm unit, that holds an organ of a patient during surgery.

(2)

The medical support arm apparatus according to (1), in which each joint unit constituting the arm unit is provided with a torque sensor that detects a torque acting on each joint unit, and a force acting on the retractor is detected on a basis of a detection value from each torque sensor.

(3)

The medical support arm apparatus according to (2), in which a driving of the arm unit is controlled so that the detected force acting on the retractor does not exceed a certain threshold value.

(4)

The medical support arm apparatus according to (2) or (3), in which a driving of the arm unit is controlled on a basis of the detected force acting on the retractor, so as to cancel out a force acting on the retractor due to a weight of the organ.

(5)

The medical support arm apparatus according to any one of (2) to (4), in which a force sensor is provided on a part where the retractor contacts the organ, and the force acting on the retractor is detected further on a basis of a detection value from the force sensor.

(6)

The medical support arm apparatus according to any one of (1) to (5), in which each joint unit constituting the arm unit is provided with a torque sensor that detects a torque acting on each joint unit, and a slippage of the organ with respect to the retractor is detected on a basis of a detection value from each torque sensor.

(7)

The medical support arm apparatus according to any one of (1) to (6), in which a force sensor is provided on a part where the retractor contacts the organ, and a slippage of the organ with respect to the retractor is detected on a basis of a detection value from the force sensor.

(8)

The medical support arm apparatus according to (6) or (7), in which in a case in which the slippage of the organ with respect to the retractor is detected, a warning is issued to a user.

(9)

The medical support arm apparatus according to any one of (1) to (8), in which a driving of the arm unit is controlled to support a movement of the arm unit in a direction of a force imparted from outside in accordance with an operation performed by a user.

(10)

The medical support arm apparatus according to any one of (1) to (9), in which during abdominal surgery, the retractor holds a body wall opened at an abdominal incision so as to spread the body wall outward and secure an opening at the abdominal incision.

(11)

The medical support arm apparatus according to any one of (1) to (9), in which during abdominal surgery, the retractor is inserted into a body cavity of the patient from an abdominal incision, and holds the organ inside the body cavity.

(12)

The medical support arm apparatus according to any one of (1) to (9), in which during endoscopic surgery, the retractor is inserted into a body cavity from an insertion opening made in a body wall of the patient, and holds the organ inside the body cavity.

REFERENCE SIGNS LIST 400, 500 support arm apparatus
410 base unit
420, 510 arm unit
421a to 421f, 511a to 511f joint units
423, 423a, 423b, 423c, 423d, 431, 701a, 701b, 809 retractor
430, 610 actuator
424, 611 motor
426, 612 reduction gear
427, 613 encoder
428, 614 torque sensor
440 control device
432 force sensor

The invention claimed is:

1. A medical support arm apparatus, comprising:
an arm unit having a plurality of joint units, each joint unit being provided with a torque sensor detecting a value of torque acting on each joint;
a retractor configured to hold an organ of a patient during surgery, the retractor being located on a distal end of the arm unit and being provided with a force sensor at contacting point to the organ; and
circuitry including a non-transitory computer readable storage, the non-transitory storage device including computer readable instructions that when executed by a processor cause the processor to:
drive at least one of the plurality of joint units of the arm unit by force control;
determine a value of force acting on the retractor based on a value of force imparted at the contacting point to the organ as detected by the force sensor of the retractor in addition to the value of torque corresponding to at least one of the plurality of joint units;
control the arm unit so that the determined value of force that acts on the retractor by the organ does not exceed a predetermined threshold so as to prevent the organ from being subjected to excessive force by the retractor; and
determine an additional value of force acting on the retractor with respect to a weight of the organ, and to control the arm unit so as to cancel the additional value of force acting on the retractor.

2. The medical support arm apparatus according to claim 1, wherein the circuitry is configured to further determine a slippage of the organ with respect to the retractor based on at least one of the value of torque corresponding to the plurality of joint units or the value of force detected by the force sensor of the retractor.

3. The medical support arm apparatus according to claim 2, wherein in a case in which the slippage of the organ with respect to the retractor is determined, the circuitry is configured to output a warning to a user.

4. The medical support arm apparatus according to claim 1, wherein the circuitry is configured to control the arm unit so as to support a movement of the arm unit in a direction of a force instructed from outside in accordance with an operation performed by a user.

5. The medical support arm apparatus according to claim 1, wherein
during abdominal surgery, the retractor is configured to hold a body wall opened at an abdominal incision so as to spread the body wall outward and secure an opening at the abdominal incision.

6. The medical support arm apparatus according to claim 1, wherein
during abdominal surgery, the retractor is configured to be inserted into a body cavity of the patient from an abdominal incision, and is configured to hold the organ inside the body cavity.

7. The medical support arm apparatus according to claim 1, wherein
during endoscopic surgery, the retractor is configured to be inserted into a body cavity from an insertion opening made in a body wall of the patient, and is configured to hold the organ inside the body cavity.

8. The medical support arm apparatus according to claim 1, wherein
the force sensor is a pressure sensor detecting contact pressure to the organ against the force sensor.

9. The medical support arm apparatus according to claim 1, wherein
the force sensor is a strain sensor detecting stress corresponding to an amount of deformation of the retractor.

10. The medical support arm apparatus according to claim 2, wherein
in a case in which the slippage of the organ with respect to the retractor is determined, the circuitry is configured to control the arm unit so as to keep holding the organ.

11. The medical support arm apparatus according to claim 10, wherein
in a case in which the slippage of the organ with respect to the retractor is determined, the circuitry is configured to control the arm unit so that the arm unit is configured to press the organ against another organ by the retractor.

* * * * *